United States Patent [19]
Hoover

[11] Patent Number: 4,943,939
[45] Date of Patent: Jul. 24, 1990

[54] SURGICAL INSTRUMENT ACCOUNTING APPARATUS AND METHOD

[76] Inventor: Rocklin Hoover, Rte. 3, Box 314x-4, Sumter, S.C. 29154

[21] Appl. No.: 237,730

[22] Filed: Aug. 29, 1988

[51] Int. Cl.⁵ .............. G06F 15/20; G01N 15/00; G06M 7/00; B65D 83/10
[52] U.S. Cl. .............. 364/555; 364/413.01; 364/479; 250/222.1; 377/6; 377/39; 128/419 R; 206/363; 221/92; 606/1
[58] Field of Search .............. 364/555, 403, 413.01, 364/479; 128/762, 303 R, 419 R, 419 N; 377/6, 39; 250/221, 222.1, 435, 576; 221/92, 155; 206/363, 370, 382

[56] References Cited
U.S. PATENT DOCUMENTS

| 2,421,782 | 6/1947 | Gibbs et al. | 221/92 |
| 3,692,985 | 6/1972 | Kalman | 377/6 |
| 3,922,532 | 11/1975 | Kitchener et al. | 364/555 |
| 4,151,913 | 5/1979 | Freitag | 206/370 |
| 4,168,001 | 9/1979 | Horvath et al. | 206/370 |
| 4,229,420 | 10/1980 | Smith et al. | 206/370 X |
| 4,342,391 | 8/1982 | Schainholz | 206/370 |
| 4,422,548 | 12/1983 | Cheesman et al. | 206/370 |
| 4,449,538 | 5/1984 | Corbitt et al. | 128/762 X |
| 4,639,875 | 1/1987 | Abraham et al. | 364/403 X |
| 4,737,910 | 4/1988 | Kimbrow | 364/403 |
| 4,812,985 | 3/1989 | Hambrick et al. | 364/403 X |
| 4,814,592 | 3/1989 | Bradt et al. | 364/479 X |

Primary Examiner—Parshotam S. Lall
Assistant Examiner—Joseph L. Dixon
Attorney, Agent, or Firm—Michael A. Mann

[57] ABSTRACT

An apparatus for accounting for surgical instruments dispensed into and withdrawn from the surgical operating environment to avoid leaving instruments in the environment comprises a plurality of instrument bearing compartments mounted on a base, a stand for storing surgical instruments after use, and a digital computer programmed to receive signals both from the compartments as a sterile instrument is dispensed and from the stand when a used instrument is stored thereon, convert the signals to numbers of instruments dispensed and stored, subtract the latter number from the former and display the difference. A non-zero different means an instrument remains in the operating environment and must be visually accounted for by operating room staff. The signal from the compartments is preferably generated an interruption of beam of light carried by fiber optic filaments when an instrument is dispensed from a compartment. The signal from the stand is a pattern of transmitted light and dark areas created by instruments stored on the stand carried by an array of fiber optic filaments or digitized video imaging carried by a transmission yoke to the digital computer for digital image decoding.

24 Claims, 4 Drawing Sheets

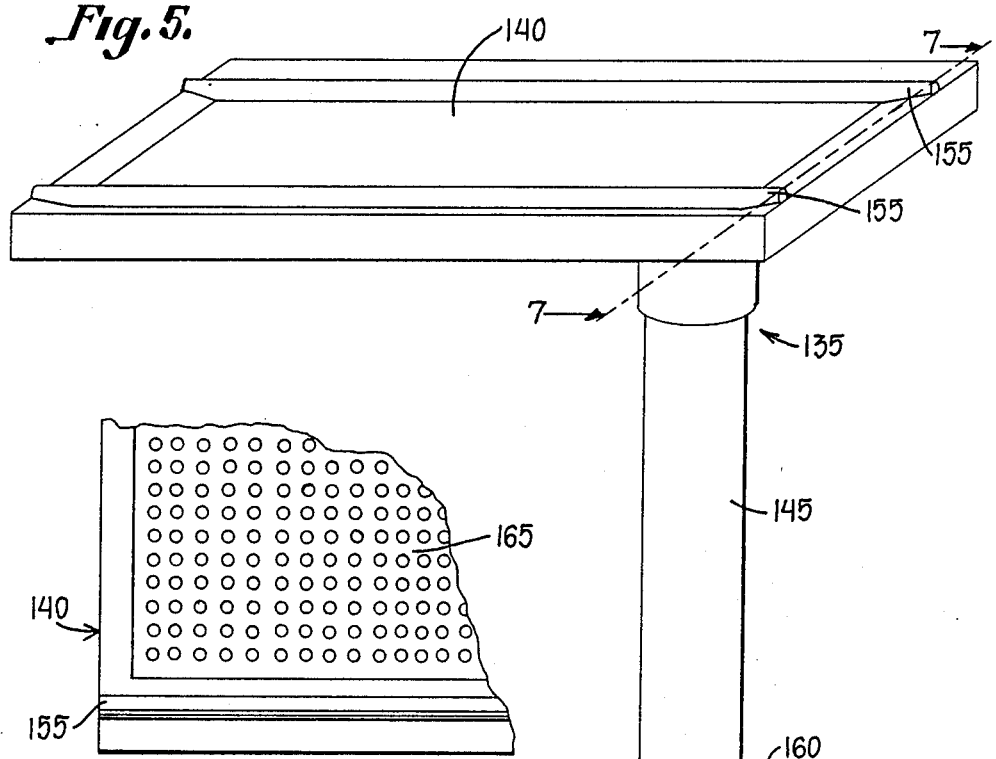
Fig. 5.
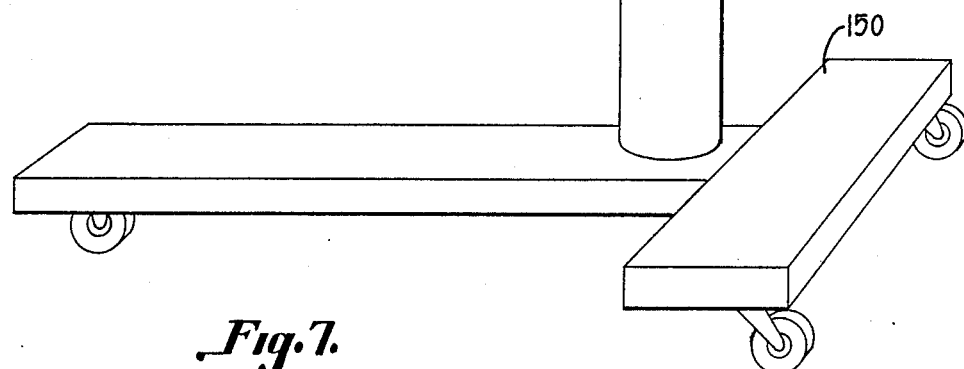
Fig. 6.
Fig. 7.
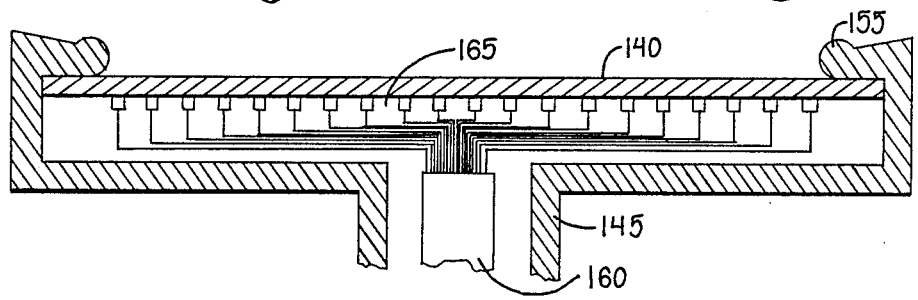

SURGICAL INSTRUMENT ACCOUNTING APPARATUS AND METHOD

BACKGROUND OF THE INVENTION

The present invention relates to apparatuses for surgical instruments. In particular, the present invention relates to an apparatus for continuously accounting for instruments that enter and leave the operating environment. In preparation for surgery, an instrument pack, or tray of surgical instruments, is brought into an operating room. Both tray and instruments have been previously sterilized in an autoclave. The instrument pack contains an assortment of instruments, including hemostats, clamps, forceps, scissors, and the like, based on the type of surgery to be performed.

A scrub nurse removes the instruments from the pack and carefully arranges them on a table, called the back table, behind the operating table. Instruments are organized in rows on rolled toweling so that they may be easily and quickly viewed and grasped during the operation for handing to the surgeon handle end first.

In the course of surgery, a large number of instruments may be used in the operating environment. Some of these are held by the surgeons or other operating staff; others, such as clamps, are in use in the patient. After use or between uses, each used instrument is set aside on a "Mayo" stand. The back table is used primarily for sterilized, unused instruments.

All instruments must be carefully accounted for at the conclusion of surgery to avoid leaving instruments in the patient.

Accounting for instruments is done three times during the operation by the nurses. The first count is done before the start of the operation; the second, at the start of closure of the patient; and the third, at the start of skin closure.

A discrepancy in the count must be resolved by additional counts, by physical examination of the patient, operating suite, or by x-ray examination if necessary. Although it is unusual for a discrepancy in the count to result from an instrument still in the patient, counting and recounting occurs in every operation. These three mandatory accountings are time consuming, tie up professional personnel, contribute to operating room suite down time, costs the hospital money, costs the insurance companies money, costs the patient money, costs the physician money, distracts personnel during the surgical procedure, lengthens the time the patient is exposed to the anesthesia thus increasing mortality/morbidity risk, and are generally distasteful to all involved. Thus, the time required for searching and accounting for surgical instruments introduced into the operating environment is critical.

The prior art contains a variety of holders for surgical instruments, typically trays for holding a stack of like instruments for sterilization but not also for dispensing and counting.

U.S. Pat. No. 3,802,555 issued to Grasty, et al., discloses a surgical instrument package and handling procedure comprising a set of trays having recessed compartments for surgical instruments. Counting is done visually and there is little flexibility in tailoring the type and number of instruments for different operations.

Freitag's Retaining and Inventory Pad for Surgical Sharps and Needles (U.S. Pat. No. 4,151,913) uses ridges with storing zones to control a limited class of surgical instruments. The instruments are counted visually.

Cheeseman, et al. disclose in U.S. Pat. No. 4,422,584 a Surgical Sponge Counter and Blood Loss Determination System having an array of pouches for used sponges about the periphery of a lined "kick" bucket.

None of the prior art patents discloses an apparatus that automatically counts the number of instruments used. None counts instruments dispensed into and removed from the operating environment. None eliminates the time, financial costs, and risk required to count and recount instruments to verify a missing instrument.

Accordingly, it is an object of the present invention to provide an apparatus for accounting for standard surgical instruments in the operating environment.

It is an object of the present invention to increase operating room suite and personnel utilization, and also decrease financial costs and patient risk.

It is another object of the present invention to provide an apparatus for determining the difference between the number of instruments dispensed into and the number received from the operating environment.

It is an object of the present invention to provide a sterilizable uniform dispenser for displaying and counting standard surgical instruments.

It is an object of the invention to provide a means for counting instruments stored on a Mayo stand.

It is an object of the invention to provide a process for determining the number of instruments entering and leaving the operating environment.

SUMMARY OF THE INVENTION

To achieve the foregoing and other objects of and in accordance with the purposes of the invention, as embodied and broadly described herein, the present invention comprises the combination of a dispenser of sterile surgical instruments, a storer of used instruments and a digital computer for receiving and decoding signals from the dispenser and the storer which decoded signals enable the computer to count the numbers of surgical instruments dispensed and received and to compare the number of instruments entering the operating environment from the dispenser to the number removed to the storer from the operating environment so that a discrepancy between these numbers, if any, can be continually known.

The dispenser comprises an array of individual compartments on a base, a rotating and displaying base or in other displaying arrangements, such as a linear or quasi-linear, "concert orchestra" arrangement. Each compartment dispenses a particular type of standard surgical instrument. The instruments are dispensed one at a time. As an instrument is withdrawn, a signal is generated, preferably by the interruption of a fiber optic light beam, and transmitted to the digital computer.

The storer is a Mayo stand modified to obtain and transmit to the digital computer a pattern of light and dark areas or a video transmission created by instruments received thereon. The bed of the modified stand comprises a large array of fiber optic filaments or video camera for transmitting the pattern.

The digital computer counts the signals from the dispenser and decodes the light array pattern or the video signal received from the modified Mayo stand. The instrument count from the dispenser and the stand are compared, a difference determined and displayed by the computer or visually from the screen. A difference means that an instrument has been introduced into but not received from, the operating environment. During an operation, the difference is equal to the number of instruments in use in the patient or in the surgeon's hands. After surgery, but before closure, any difference indicates a missing instrument which must be visually accounted for by operating room staff. That number is accurately and continually determined without much effort on the part of the operating room staff.

The advantage of the present invention lies in the elimination of the time for counting and recounting of instruments. The uniform dispensers also eliminate the time required by the scrub nurse to arrange the instruments on the table behind the operating table since the dispensers are already arranged on the base for rapid dispensing.

Reference is now made in detail to the present preferred embodiment of the invention, an example of which is illustrated in the accompanying drawings.

BRIEF DESCRIPTION OF THE DRAWINGS

The accompanying drawings, which are incorporated in and form a part of the specification, illustrate the invention and, together with the description, serve to explain the principles of the invention. In the drawings:

FIG. 5 is a perspective view of the modified Mayo stand;

FIG. 6 is a portion of a top plan view of the modified Mayo stand according to the invention;

FIG. 7 is a cross sectional view of the surface of the modified Mayo stand along lines 7—7 of FIG. 5.

DETAILED DESCRIPTION OF A PREFERRED EMBODIMENT

The present invention is a combination of three components interconnected to form a system to account for surgical instruments introduced into the operating environment. The important value to be ascertained by the digital computer, based on electrical signals received, is a discrepancy, if any, between the number of sterile instruments dispensed into the operating environment from a plurality of compartments and the number of used instruments received from the operating environment for storing on a modified Mayo stand.

Instruments are in the operating environment if they are in the hands of surgeons performing the operation, in the patient, or held by surgical staff attending to the surgeon. Instruments are out of the operating environment if they have not been dispensed or are stored on the modified Mayo stand.

To ascertain the number of surgical instruments in the operating environment, a count of instruments entering the environment is made by digital means, preferably by a computer programmed to count the interruptions in a beam of light or other energy beam caused by the dispensing of instruments. A second count is made of instruments received from the operating environment by another digital or visual means, preferably by a computer scanning a digital image of dark and light areas created by the instruments placed on the modified Mayo stand. Alternately, a computerized digital video image may be created using classical video equipment and techniques to create a digital video pattern of the instrument. The second count is subtracted from the first and the difference displayed continually by a digital computer in accordance with well known automatic processing techniques. A visual check of the Mayo stand may be made by calling to the computer screen the actual video transmission.

Figure 1:
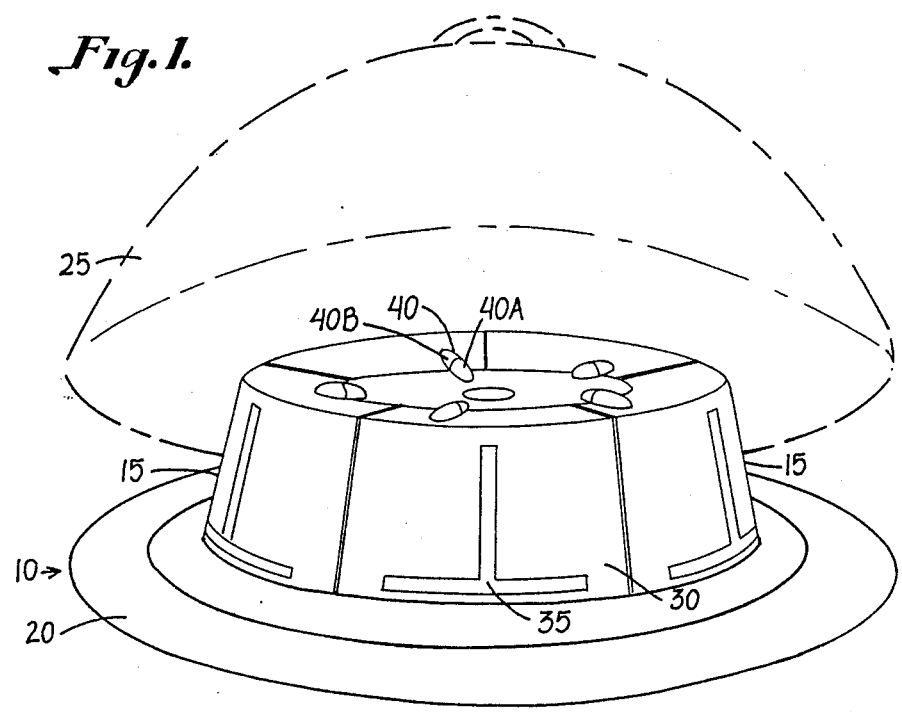
FIG. 1 is a perspective view of the dispenser showing five instrument compartments on the base with the autoclave dome in the partially raised position.

Referring now to FIG. 1, the dispenser 10 comprises a plurality of compartments 15 seated on a base 20. FIG. 1 shows five compartments 15. Base 20 is preferably circular and rotatable and may seat one or more tiers of compartments but may be formed in other displaying arrangements, such as a linear or quasi-linear, "concert orchestra" arrangement. Base 20 with compartments 15 may be sterilized in an autoclave dome 25 shown in FIG. 1 partially raised.

Each compartment 15 comprises a shell 30 for housing one type of standard surgical instrument, a slot 35 in shell 30 through which slot 35 surgical instruments are dispensed one at a time, and a fiber optic filament aligner 40 having a base part 40A and a compartment part 40B.

Figure 2:
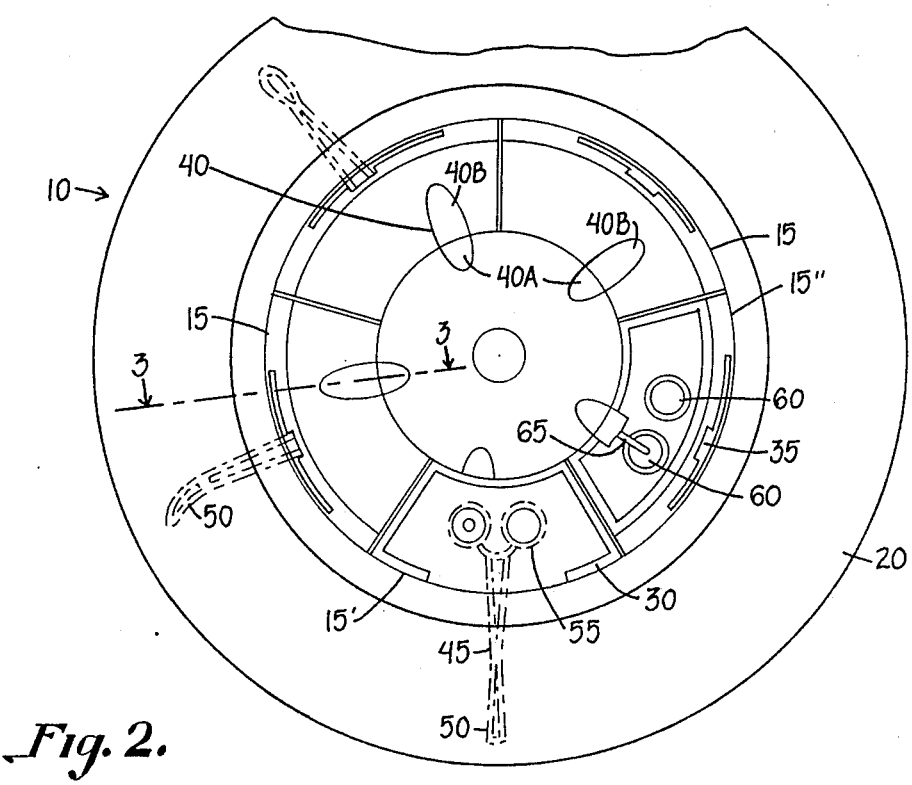
FIG. 2 is a top plan view of the dispenser shown with five instrument compartments, two of which having portions cut away.

FIG. 2 illustrates the relationship of compartments 15 in a top plan view of dispenser 10. Surgical instruments 45 extend through slots 35 so they are visible and readily graspable by the scrub nurse. A functional end 50 rather than the handle end 55 of the instruments 45 extends through slots 35 so that the scrub nurse hands instrument 45 to the surgeon handle end 55 first, in accordance with operating procedure. Also, it is easier to distinguish and select instruments 45 by their functional ends 50 since many instruments have similar, scissors-like handle ends 55.

The partially cut away view of the top of shell 30 of one of compartments 15' in FIG. 2 shows the interior of that compartment 15'. Two masts 60 for holding handle end 55 are seen inside shell 30 of compartment 15". A first fiber optic filament 65 runs through the compartment part of fiber optic filament aligner 40B to a position over one of masts 60, then down through mast 60.

Figure 3:
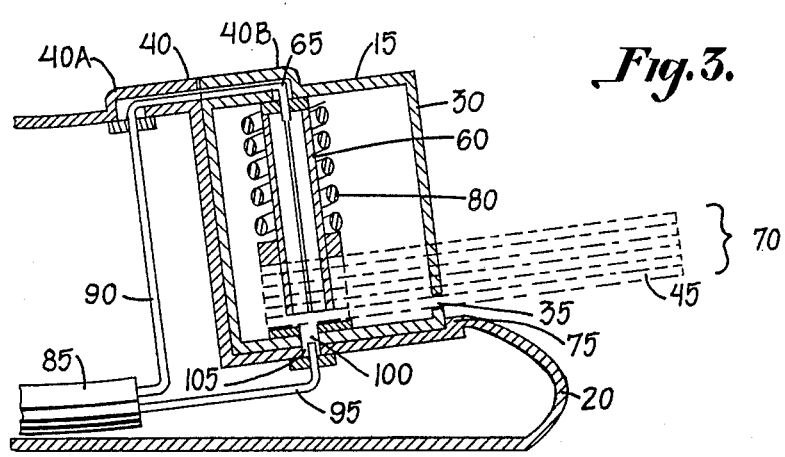
FIG. 3 is a cross sectional view along lines 3—3 of FIG. 2.

FIG. 3, a cross-sectional side view of compartment 15, shows base 20 of dispenser 10 curving down and away from a stack of instruments 70 for ease in grasping the bottom instrument 45 of stack 70. Base 20 has a lip 75 to help seat compartment 15 on base 20 and align base part 40A with compartment part 40B of filament aligner 40.

Extending from within shell 30 through slot 35, stack 70 is held in place by masts 60 which depend from the top of compartment 15 through handle ends 55 of instruments 45, except for handle end 55 of the bottom instrument 45 in stack 60. A spring 80 urges stack 60 downwardly so that the bottom instrument 45 in stack 60 is always positioned for removal from shell 30 through slot 35.

A first fiber optic harness 85 carries a second fiber optic filament 90 to each compartment 15 from the base part of fiber optic filament aligner 40A. Second fiber optic filament 90 is aligned with first filament 65 to transmit light thereto. First filament 65 runs into shell 30 and through mast 60, terminating just short of the end of mast 60.

A third fiber optic filament 95 runs from first harness 85 to a position in base 20 directly under the end of first filament 65 where a first hole 100 in base 20 and a second hole 105 in shell 30 of compartment 15 are aligned so that light transmitted from first filament 65 can be received by third filament 95.

Figure 4:
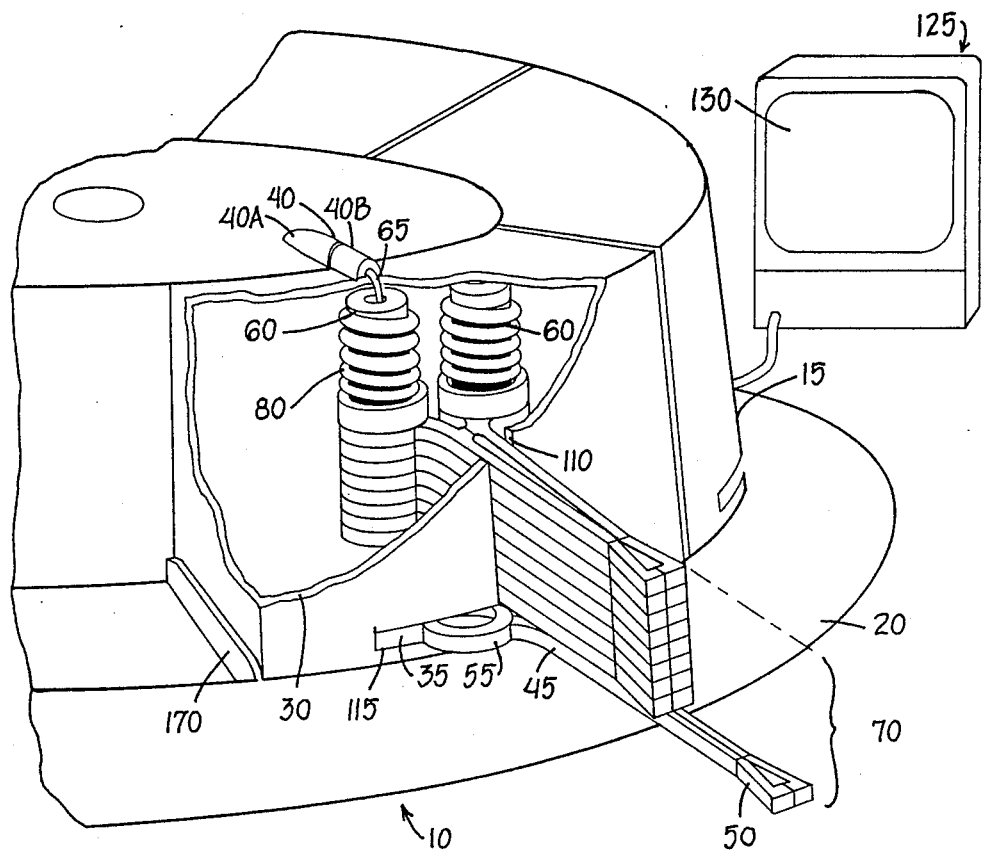
FIG. 4 is a detailed perspective view of the computer and the dispenser with one compartment removed and the adjacent compartment having a portion cut away.

In FIG. 4, stack 70 is shown in perspective with instrument 45 at the bottom of stack 70 issuing through slot 35. Slot 35 has a vertical portion 110 and a horizontal portion 115 so that the functional ends of the instruments 45 in stack 60 can extend beyond compartment 15 but only one instrument 45, the bottom one, can issue through slot 35.

Between every compartment 15 is a positioning key 170 for seating adjacent compartments 15, to align first filament 65 and second filament 90, and to align first and third filaments 65 and 95.

As instrument 45 is pulled through slot 35, handle end 55 passes across the bottom of mast 60 and between first filament 65 and second filament 90. The interruption of light is electronically perceived by digital computer 125 to which first harness 85 is connected and the interruption counted as the dispensing of a single instrument into the operating environment.

The modified Mayo stand 135, shown in FIG. 5 has a transparent surface 140 supported by a pedestal 145 on a rolling base 150. Surface 140 has edges 155 raised for elevating instruments 45 placed thereon between uses and after use. A second harness 160 enters Mayo stand 135 at pedestal 145.

FIG. 6 shows an array of fiber optic filaments 165 in surface 140. Array 165 must contain a sufficient number of filaments to receive a detailed image of transmitted dark and light pattern created by the instruments stored on surface 140 and to enable digital computer 125 to recognize images and count the images recognized when digital computer 125 is programmed with digital imaging and pattern recognition logic and counting software. For example, a circular pattern of darkness approximately 2-3 centimeters in diameter is recognizable as part of handle end 55 of an instrument, and its identity confirmed by cross-referencing against several other positions where light or dark areas would be expected to exist on the same instrument. In addition, FIG. 6 may house a video camera that would transmit digitized video images to digital computer 12 for pattern recognition logic and counting. This digitized video transmission could also be called to screen 130 for visual examination.

FIG. 7, a cross sectional view of surface 140, shows array 165 collected into second harness 160 at pedestal 145.

Figure 8:
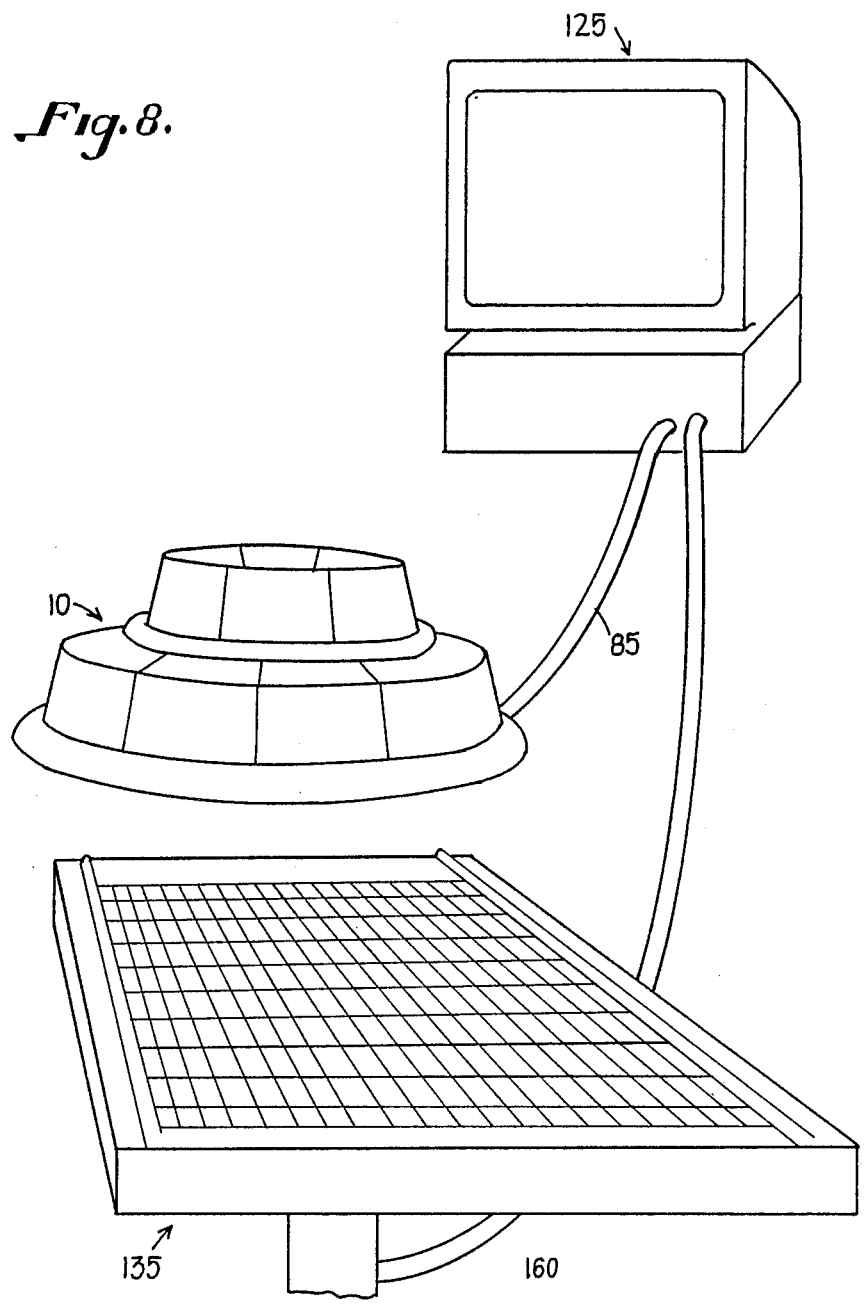
FIG. 8 shows a two-tiered dispenser and modified Mayo stand interconnected to the digital computer.

FIG. 8 shows dispenser 10, computer 125 and modified Mayo stand 135 interconnected by fiber optic first harness 85 and second harness 160, respectively.

In use, the surgical instrument accounting apparatus continually displays the number of instruments in the operating environment. At the end of the operation but before closure, the number displayed must be equal to the number of instruments in the surgeon's hands for closure, if any. It is useful for the surgeon to hand all instruments to the scrub nurse to store on the modified Mayo stand so that the accounting can be done. A non zero count displayed on the screen of the computer requires investigation.

Before skin closure, a quick check of the screen can confirm all instruments are accounted for. No counting of instruments need be done by operating room staff. Particularly in large, long operations, considerable time can be saved in counting the many surgical instruments.

The foregoing description of the preferred embodiments of the invention has been presented for purposes of illustration and description. It is not intended to be exhaustive or to limit the invention to the precise form disclosed, and obviously many modifications and variations are possible in light of the above teachings. The embodiments were chosen and described in order to best explain the principles of the invention and its practical application to thereby enable one skilled in the art to best utilize the invention in various embodiments and with various modifications as are suited to the particular use contemplated. It is intended that the scope of the invention be defined by the claims appended hereto.

What is claimed is:

1. An apparatus for accounting for standard surgical used during surgery, such as clamps, hemostats and the like, dispensed into and removed for storage out of an operating environment to avoid leaving surgical instruments in said operating environment, said apparatus comprising:
    a means for dispensing surgical instruments into said operating environment, said dispensing means having a first signalling means for signalling a dispensing of one of said surgical instruments;
    a means for storing surgical instruments withdrawn from said operating environment, said storing means having a second signalling means for signalling a storing of one of said surgical instruments; and
    a computer means connected to said dispensing and said storing means for receiving said signaled dispensing and said signaled storing of said surgical instruments, for computing a first number anD a second number of said surgical instruments dispensed into and received for storing out of said operating environment, respectively, and for subtracting said second number from said first number to determine a third number of said surgical instruments that have been dispensed by said dispensing means into said surgical environment but are not being stored by said storing means out of said surgical environment.

2. The apparatus of claim 1 wherein said dispensing means further comprises:
    a plurality of containers for holding said surgical instruments; and
    a base for seating and displaying said containers.

3. The apparatus of claim 2 wherein said first signalling means further comprises optical fibers for carrying light beams, said optical fibers positioned within said containers so that said dispensing of said surgical instruments interrupts said light beams thereby indicating to said computer means that said surgical instruments have entered said operating environment.

4. The apparatus of claim 2 wherein said base has a seating means for positioning said compartments thereon so that said series of fiber optic filaments are aligned.

5. The apparatus of claim 2 wherein said containers dispense said surgical instruments one at a time, said surgical instruments having a functional end and a handle end.

6. The apparatus of claim 5 wherein said containers dispense said surgical instruments by said functional ends first.

7. The apparatus of claim 6 wherein said containers display a stack of surgical instruments so that said stack of surgical instruments in said compartments are visible.

8. The apparatus of claim 7 wherein said base is formed to allow said surgical instruments to be removed only from the bottom of said stack.

9. The apparatus of claim 1 wherein said storing means further comprises:
   a stand; and
   a surface mounted on said stand for storing said surgical instruments thereon, out of said operating environment, said surface having said second signalling means for signalling said second number of surgical instruments to said computer means.

10. The apparatus of claim 9 wherein said stand includes:
    a rolling base;
    a pedestal mounted on said rolling base; and
    said surface being mounted on said pedestal.

11. The apparatus of claim 9 further comprising a fiber optic filament array mounted within said surface of said storing means for receiving a pattern of light and dark formed by light shining on said surface having surgical instruments thereon.

12. The apparatus of claim 9 further comprising a video transmission yoke mounted within said surface of said storage means for receiving a video image of surgical instruments thereon.

13. The apparatus of claim 1 wherein said computer means processes a first signal from said first signalling means and a second signal from said second signalling means wherein the process comprises the steps of decoding said first signal into said first number of surgical instruments and displaying said first number;
    decoding said second signal into said second number of surgical instruments and displaying said first number;
    subtracting said second number from said first number to obtain a difference; and
    displaying said difference.

14. The apparatus of claim 13 wherein said computer means has pre-programmed images and the step of decoding said second signal further comprises the steps of scanning said second signal to find an image if any;
    comparing said image if any found in said second signal with said pre-programmed images;
    identifying said image as produced by one of said surgical instruments; and
    counting said image.

15. The apparatus of claim 12 wherein said computer means provides for programmed screen display of video images for visual examination.

16. An apparatus for accounting for standard surgical instruments used during surgery, such as clamps, hemostats and the like, introduced into and removed from an operating environment to avoid leaving surgical instruments in said operating environment, said apparatus comprising:
    a plurality of compartments for dispensing said surgical instruments;
    a base for seating and displaying said compartments thereon;
    a first signalling means for signalling a dispensing of a first number of said surgical instruments, said signalling connected to said compartments;
    a stand having a surface for storing said surgical instruments, said stand having a second signalling means for signalling a second number of surgical instruments stored on said surface of said stand; and
    a computer means connected to said first signalling means and said second signalling means for determining said first and said second numbers of said surgical instruments, subtracting said second number from said first number to determine a difference between said numbers and displaying said difference.

17. The apparatus of claim 16 wherein said first signalling means further comprises a plurality of fiber optic filaments for carrying light beams, said filaments running from said base and said plurality of compartments to said computer means, said dispensing of said surgical instruments causing interruptions in said light beam whereby said computer means can determine said first number of said surgical instruments.

18. The apparatus of claim 17 wherein said second signalling means includes means for generating a pattern of said surgical instrument placed on said stand.

19. The apparatus of claim 18 wherein said second signalling means transmits a contrast pattern of light and dark areas from said second number of surgical instruments stored on said surface.

20. The apparatus of claim 19 wherein said contrast pattern is created by an array of fiber optic filaments carried by said surface and connected to said computer means so that said computer means can determine said second number of said surgical instruments.

21. The apparatus of claim 19 wherein said computer means is programmed to count said interruptions in said light beam signalled by said dispensing of said surgical instruments and to recognize and count images of surgical instruments in said contrast pattern signalled from said surface by said fiber optic array.

22. The apparatus of claim 16 wherein said compartments further comprise:
    a shell;
    a means for holding a stack of said surgical instruments within said shell, each of said surgical instruments of said stack having a functional end and a handle end; and
    a slot in said shell for dispensing said surgical instruments therethrough, said slot having a vertical portion and a horizontal portion, said functional end of said stack extending through said vertical portion so that said stack is visible but cannot be dispensed through said vertical portion, said surgical instruments dispensed only through said horizontal portion one at a time.

23. A method for accounting for surgical instruments used in an operating environment during an operation to avoid leaving said surgical instruments in said operating environment wherein the method comprises the steps of:
    counting by a first digital means a number of said surgical instruments dispensed into said operating environment from a dispensing source of sterile instruments;
    counting by a second digital means a second number of said surgical instruments received by a storing means located out of said operating environment;
    subtracting said second number from said first number to obtain a difference; and
    displaying said difference continually throughout said operation.

24. A method for accounting for surgical instruments used in an operating environment during an operation to avoid leaving said surgical instruments in said operating environment wherein the method comprises the steps of:

dispensing said surgical instruments from a dispenser;

generating a dispensed instrument signal each time a surgical instrument is dispensed from said dispenser;

storing said surgical instruments after removal from said operating environment and generating stored instrument signals corresponding to each of said stored surgical instruments;

transmitting said dispensed instrument signals and stored instrument signals to a computer means;

processing said dispensed instrument signals and stored instrument signals in said computer means to determine whether or not the number of dispensed instruments is equal to the number of stored instruments; and generating a differential signal representing the difference between the number of instruments dispensed and the number of instruments stored and displaying an indication of said differential signal.

* * * * *